(12) United States Patent
Ratner

(10) Patent No.: US 6,584,974 B1
(45) Date of Patent: *Jul. 1, 2003

(54) PATIENT ESOPHAGEAL DETECTOR DEVICE IN COMBINATION WITH A CARBON DIOXIDE DETECTOR

(75) Inventor: Jeffrey B. Ratner, Pinellas Park, FL (US)

(73) Assignee: Mercury Enterprises, Inc., Clearwater, FL (US)

( * ) Notice: Subject to any disclaimer, the term of this patent is extended or adjusted under 35 U.S.C. 154(b) by 5 days.

This patent is subject to a terminal disclaimer.

(21) Appl. No.: 10/008,829

(22) Filed: Dec. 7, 2001

(51) Int. Cl.[7] .............................. A62B 7/00; A62B 9/00
(52) U.S. Cl. ............................ 128/205.23; 128/207.14; 604/912
(58) Field of Search .......... 128/200.26, 207.14–207.18, 128/205.23; 604/37, 75, 132, 133, 212, 516, 910, 911, 912; 506/196

(56) References Cited

U.S. PATENT DOCUMENTS

| | | | | |
|---|---|---|---|---|
| 4,520,812 A | * | 6/1985 | Freitag et al. | 128/204.25 |
| 4,691,701 A | | 9/1987 | Williams | |
| 4,790,327 A | * | 12/1988 | Despotis | 600/532 |
| 4,928,687 A | * | 5/1990 | Lampotang et al. | 128/207.14 |
| 5,005,572 A | | 4/1991 | Raemer et al. | |
| 5,124,129 A | * | 6/1992 | Riccitelli et al. | 422/56 |
| 5,156,159 A | * | 10/1992 | Lampotang et al. | 600/532 |
| 5,197,464 A | | 3/1993 | Babb et al. | |
| 5,291,879 A | | 3/1994 | Babb et al. | |
| 5,360,003 A | * | 11/1994 | Capistrano | 128/207.15 |
| 5,375,592 A | * | 12/1994 | Kirk et al. | 128/207.14 |
| 5,400,770 A | * | 3/1995 | Nakao et al. | 604/96 |
| 5,445,160 A | * | 8/1995 | Culver et al. | 600/532 |
| 5,468,451 A | | 11/1995 | Gedeon | |
| 5,487,731 A | * | 1/1996 | Denton | 604/100 |
| 5,591,130 A | * | 1/1997 | Denton | 604/100 |
| 5,749,358 A | * | 5/1998 | Good et al. | 128/205.23 |
| 5,785,051 A | * | 7/1998 | Lipscher et al. | 128/207.15 |
| 5,846,836 A | | 12/1998 | Mallow | |
| 5,885,248 A | * | 3/1999 | Denton | 604/100 |
| 5,965,061 A | | 10/1999 | Larsson et al. | |
| 6,149,603 A | * | 11/2000 | Parker | 600/532 |
| 6,202,646 B1 | * | 3/2001 | Camadeca et al. | 128/207.14 |
| 6,502,573 B1 | * | 1/2003 | Ratner | 128/207.17 |

* cited by examiner

Primary Examiner—Weilun Lo
Assistant Examiner—Joseph F. Weiss, Jr.
(74) Attorney, Agent, or Firm—Larson & Larson, P.A.; James E. Larson

(57) ABSTRACT

The $CO_2$ detector has a disc attached to a rim which in turn is attached to a third port on a esophageal detector housing. A baffle rises from an interior surface of the housing to slightly below an opening to the third port. A first and second port of the housing on each side of the third port are in axial alignment. The first port is attached to an elastomeric bulb and the second port is adapted to be connected to an adapter which in turn is attached to an intubation tube. A colorimetric indicator paper is shown through a clear plastic cover after removing backing on the indicator paper through the second port.

15 Claims, 8 Drawing Sheets

PATIENT ESOPHAGEAL DETECTOR DEVICE IN COMBINATION WITH A CARBON DIOXIDE DETECTOR

FIELD OF THE INVENTION

This invention relates to carbon dioxide ($CO_2$) detectors. More particularly, it refers to a housing containing $CO_2$ colorimetric indicator paper, the housing attached to a bulb style esophageal detector device for detecting $CO_2$ levels in the aspirated air from a patient following intubation.

BACKGROUND OF THE INVENTION

U.S. Pat. No. 4,691,701 describes an early portable $CO_2$ detector in the form of a transparent disc containing a chemical substance exhibiting a color change indication when exposed to carbon dioxide from a patient.

U.S. Pat. Nos. 5,197,464 and 5,291,879 describe methods of monitoring $CO_2$ levels in a patient using a reversible indicator solution so that the indicator changes color continuously with the breathing of a patient.

Other references that include references to $CO_2$ color change devices are U.S. Pat. Nos. 4,790,327; 4,928,687; 4,994,117; 5,005,572; 5,166,075, 5,179,002; 5,846,836 and 5,965,061.

A critical step in the intubation of a patient is a determination that the intubation tube or endotracheal tube is placed in the trachea and not in the esophagus. If the tube is in the esophagus, there is no return of $CO_2$ beyond ambient levels from a patient's aspirated air. If the tube is in the trachea, $CO_2$ will be present up to about five percent concentration.

The trachea is substantially rigid because it is made up of C-shaped ridges of rigid cartilagineous rings joined vertically by fibro elastic tissue. The esophagus, on the other hand, is a fibro muscular tube having no intrinsic structure to maintain any rigidity. The use of a bulb at the end of the often used and well known esophageal detector device is based on the principal that the esophagus will collapse when a negative pressure is applied to its lumen, whereas a trachea will not because of its greater rigidity. Normally, an intubation tube is placed in the patient's trachea and a soft rubber bulb is compressed and then attached at one end of the intubation tube. The tube will aspirate gas freely from the patient's lungs without any resistance if the tube is in the trachea when the bulb is released. If the intubation tube is in the esophagus, the negative pressure caused by the bulb will cause the esophagus to collapse and the bulb will stay compressed. Misplacement of the intubation tube can affect the mortality of the patient.

Since it is common in emergency situations for less highly skilled technicians to apply intubation tubes for maintaining the patient's airway, it is important to have a portable single patient device confirming the proper initial placement of the intubation tube. A $CO_2$ detector serves this purpose. Although $CO_2$ detector's exist, the use with an esophageal detector device to provide confirmation of proper intubation tube placement is not known. Such a combined device exhibiting ease of use, low cost and connection to existing breathing apparatus is needed.

SUMMARY OF THE INVENTION

The invention described herein is an improvement over existing esophageal detector devices used for verifying placement of an intubation tube in a patient's trachea. The $CO_2$ detector employed in this invention has an easily mountable colorimetric indicator paper that changes color in response to $CO_2$ levels in aspirated air from a patient. It is easily mountable in communication with an esophageal detector device housing, is lightweight and gives easily readable and reliable $CO_2$ detection to confirm intubation tube placement in the patient's trachea.

The preferred $CO_2$ detector is a clear plastic disc mounted on a rim. Indicator paper is mounted on the inside surface of the plastic disc. Backing paper on the indicator paper is removed prior to use of the detector by pulling on the backing paper protruding from a port in a cylindrical housing on which the rim of the disc is mounted. The backing paper insures that the indicator paper will not be exposed prior to use. The disc rim is glued or heat welded to the esophageal detector housing. A baffle is mounted on an inner wall of the esophageal detector housing between a first and second axially positioned port. The first port is connected to an elastomeric bulb and the second port is connected to an intubation tube adapter leading to an intubation tube for insertion in a patient's trachea. Provided the tube is properly placed, the aspirated air from the patient will cause a color change on the colorimetric indicator paper viewed through the clear plastic cover of the $CO_2$ detector of this invention.

BRIEF DESCRIPTION OF THE DRAWINGS

The invention can be best understood by those having ordinary skill in the art of patient intubation by following the detailed description when considered in conjunction with the accompanying drawings in which.

DETAILED DESCRIPTION OF THE INVENTION

Figure 2:
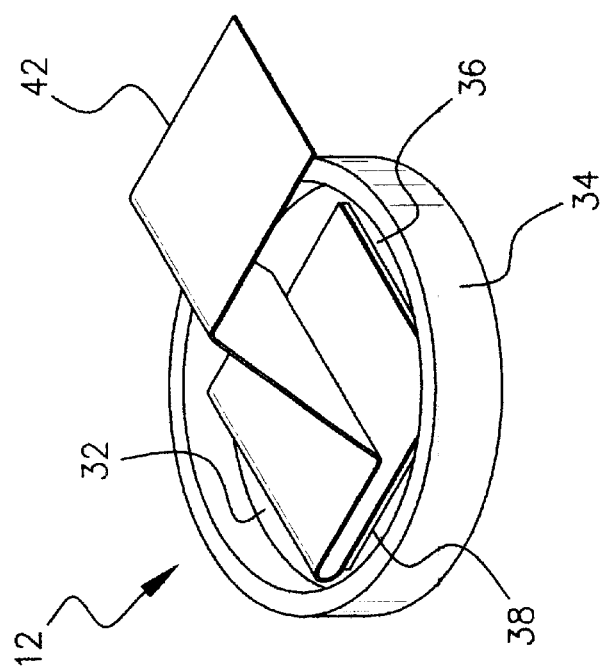
FIG. 2 is a perspective view of folded indicator paper backing prior to insertion into a port of the housing.

Throughout the following detailed description, the same reference numerals refer to the same elements in all figures.

Figure 3:
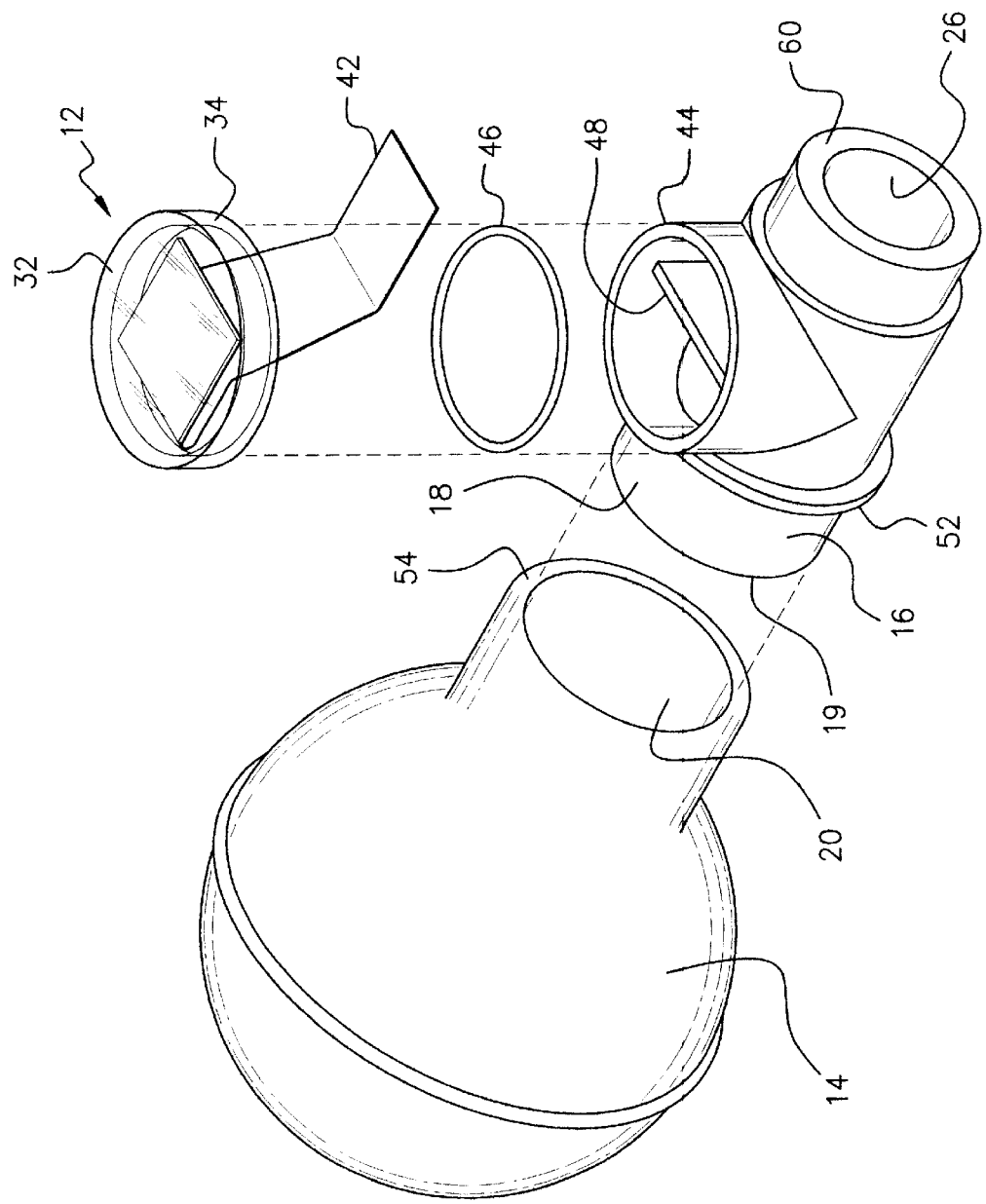
FIG. 3 is an exploded view in perspective of the bulb and housing components in the esophageal detector device with the $CO_2$ detector.
Figure 6:
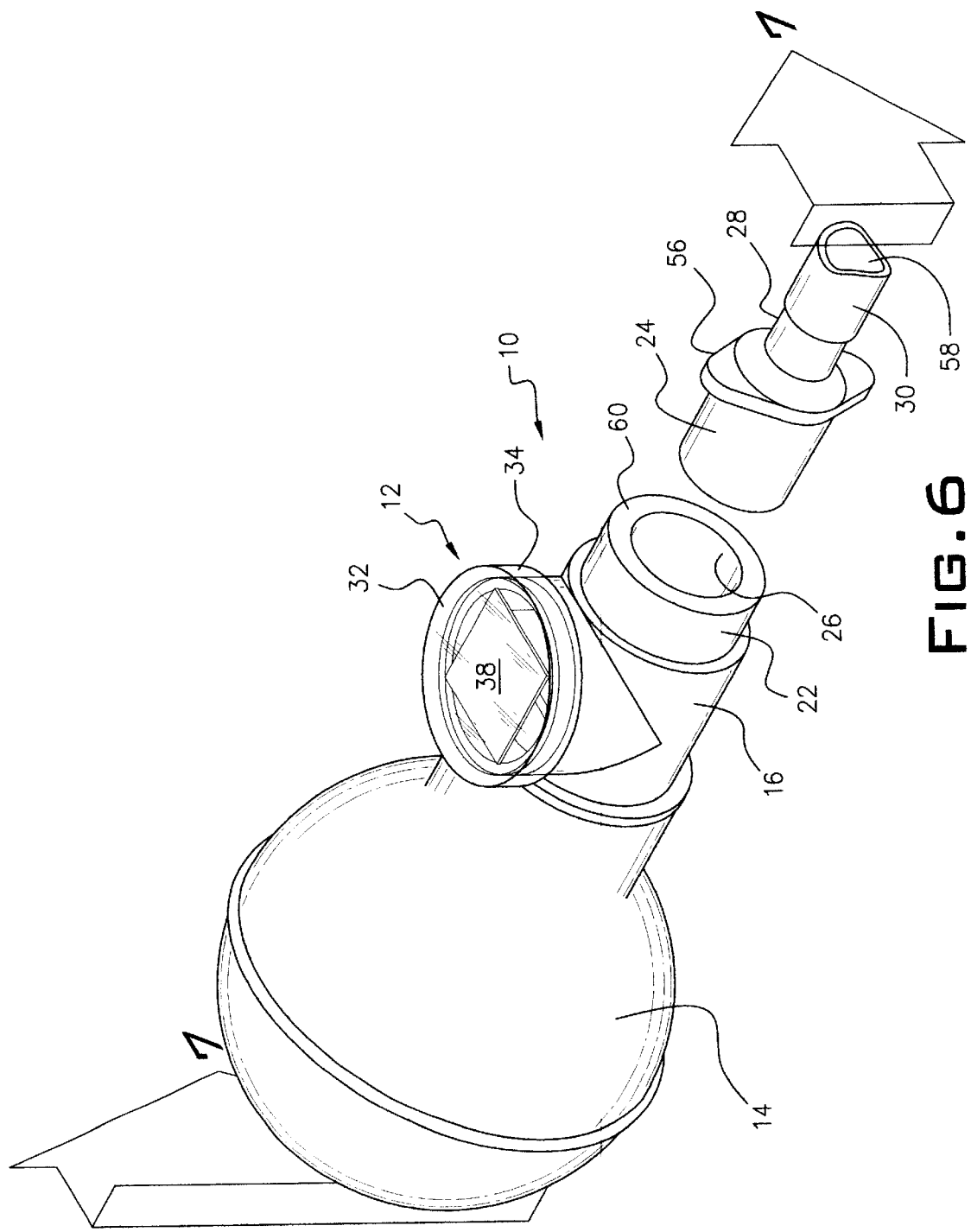
FIG. 6 is a perspective view of the intubation tube adapter being inserted in a port of the esophageal detector housing.
Figure 7:
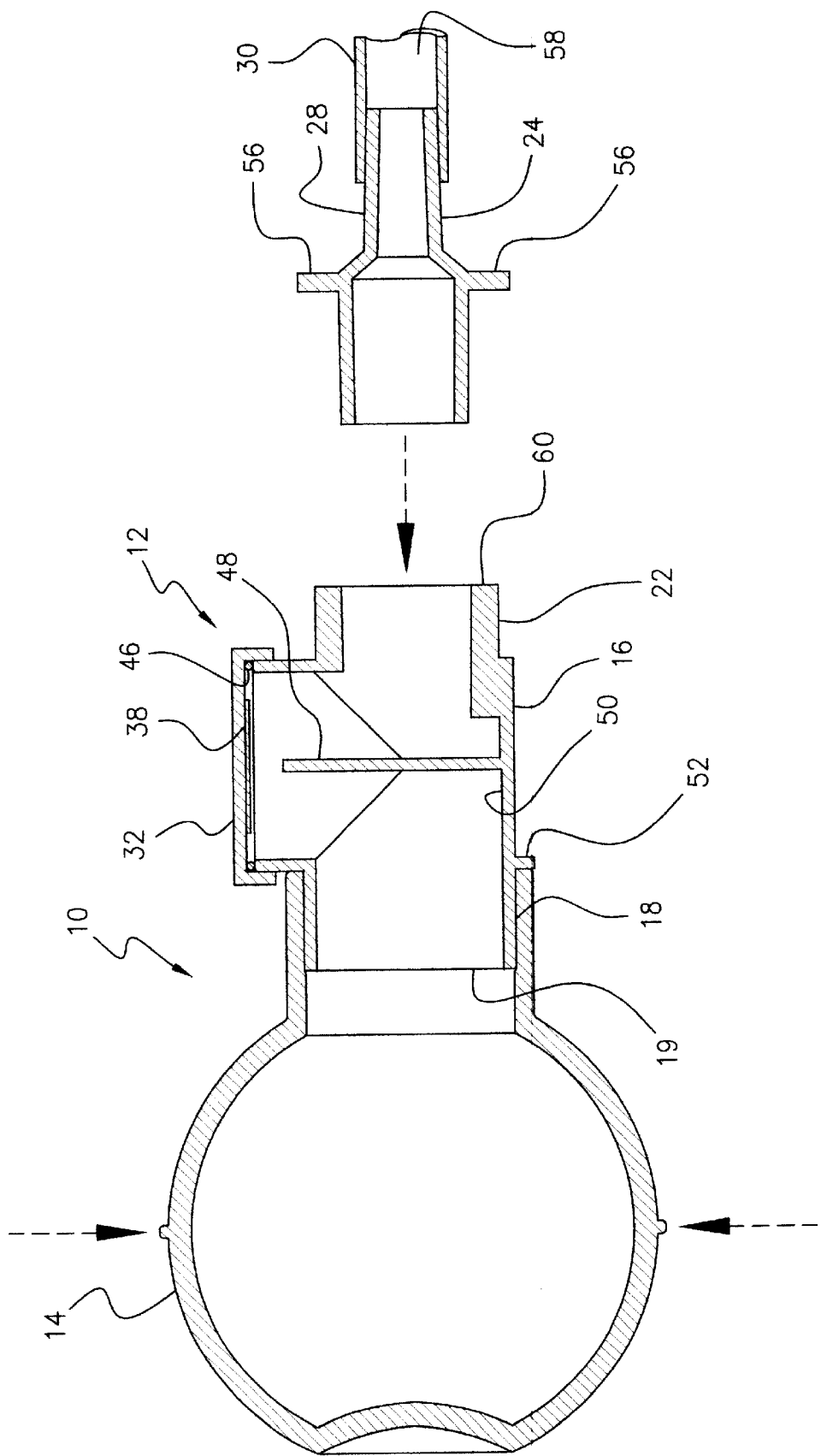
FIG. 7 is an elevational view in section of the combined $CO_2$ detector and esophageal detector device of FIG. 6 along lines 7—7.

The esophageal detector device 10 with $CO_2$ detector 12 of this invention shown in FIG. 6 has several principal components as shown in FIGS. 3 and 6. The detector device 10 has a soft elastomeric bulb 14 at a first end of a housing 16.

The housing 16 is preferably in the form of a hollow cylinder attached at a first end 18 at a first port 19 to the elastomeric bulb 14 through opening 20 and at a second end 22 to an intubation tube adapter 24 through second port 26. The first and second ports are preferably axially aligned. Alternatively, housing 16 can have an elliptical, square or other practical geometric shapes and the first and second ports can be offset from each other. The adapter 24 has a tapered insertion end 28 for engagement with an intubation tube 30 as seen in FIG. 6.

Figure 1:
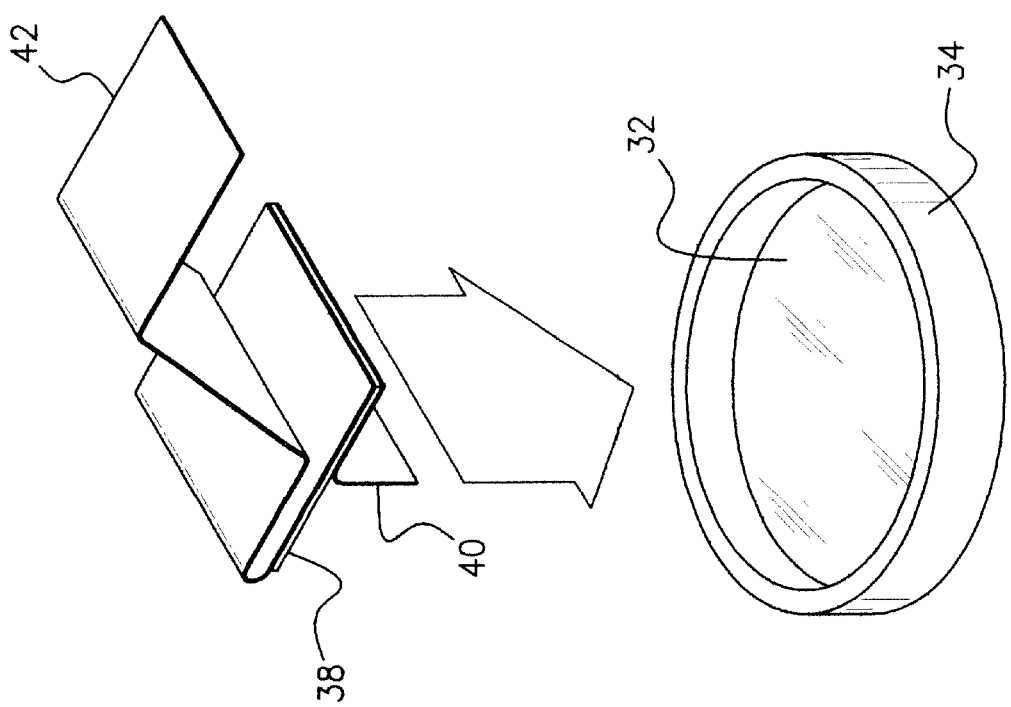
FIG. 1 is an exploded view in perspective of the indicator paper being affixed to a bottom surface of a disc for the $CO_2$ detector of the invention.

The $CO_2$ detector 12 shown in FIGS. 1 and 2 has a clear plastic disc 32 attached to an annular rim 34. Alternatively, the disc can be clear glass. A colorimetric indicator paper 38 or other chemically impregnated substrate is affixed to a bottom surface 36 of the disc 32. In the case of indicator paper, it is affixed by glue after first removing a bottom section of backing paper 40 as seen in FIG. 1. Another section of backing paper 42 is folded downwardly as shown in FIG. 3 and passes out through second port 26 in housing 16. The rim 34 is glued, snap-fit or heat welded over a top rim 44 of housing 16. An O-ring 46 seals the $CO_2$ detector rim 34 to the housing rim 44. Alternatively, the colorimetric indicator paper can be a saturated paper containing a $CO_2$ sensitive color change chemical.

A vertically placed baffle 48 is integral with interior surface 50 of housing 16. Such baffle 48 protrudes upwardly to a position slightly below rim 44.

The elastomeric bulb 14 is attached to first end 18 of housing 16 as seen in FIG. 3. A flange 52 acts as a stop against edge 54 of the elastomeric bulb 14. The intubation tube adapter 24 is inserted into the second port 26. The flange 56 may engage edge 60 of the housing 16. The tapered end 28 of the adapter 24 fits into an opening 58 of an intubation tube 30.

Figure 4:
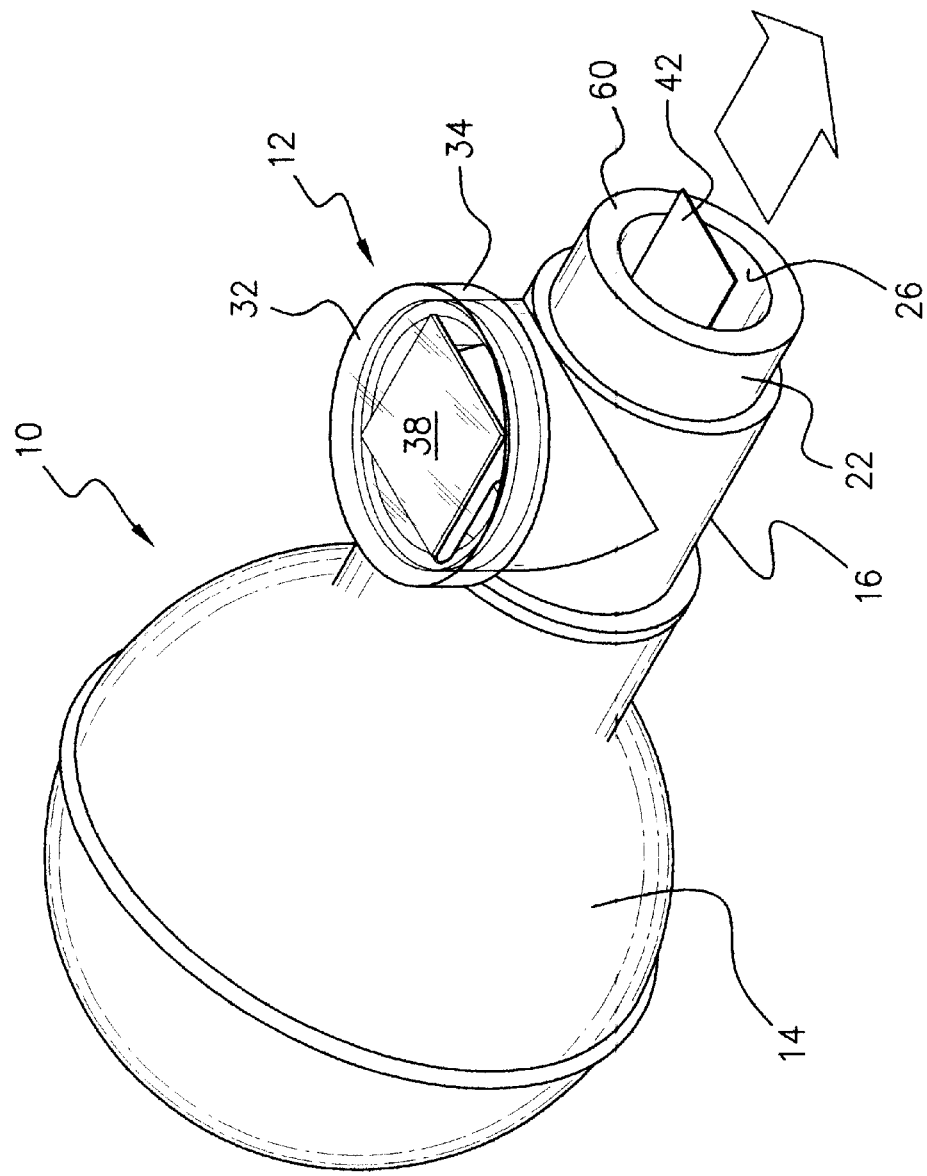
FIG. 4 is a perspective view of the indicator paper backing inserted into a port on the esophageal detector housing.
Figure 5:
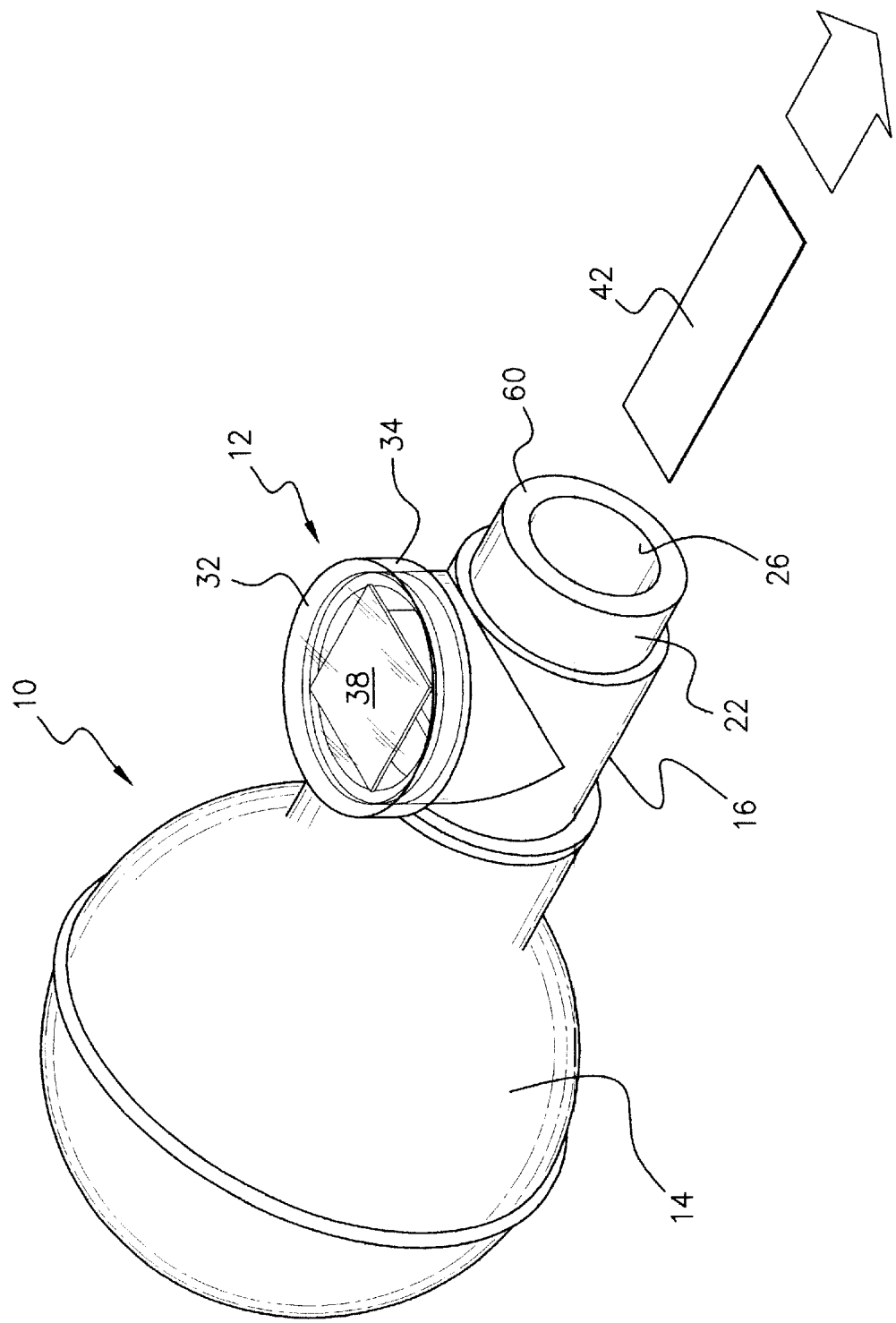
FIG. 5 is a perspective view of the backing paper being removed from the $CO_2$ detector.
Figure 8:
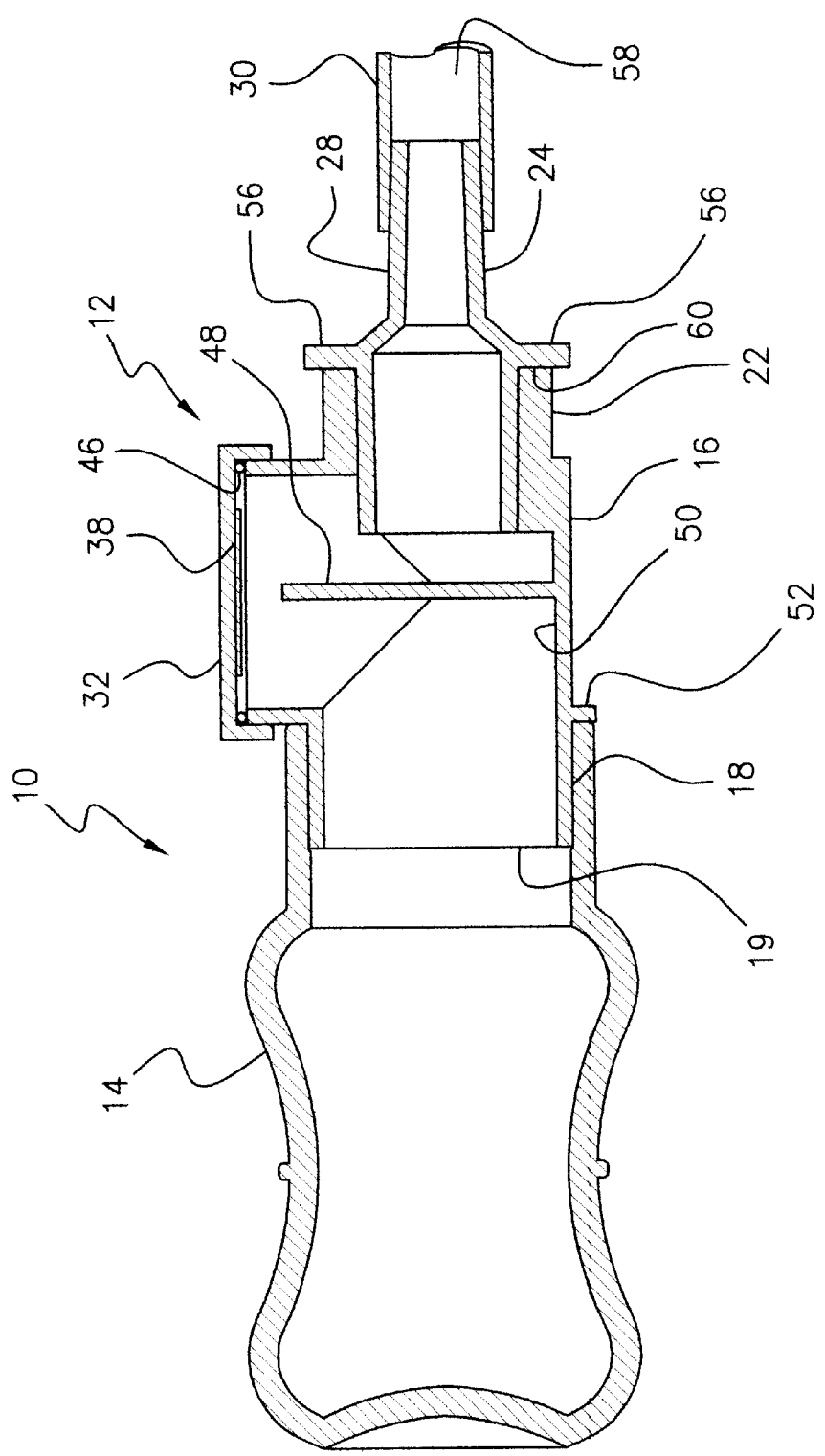
FIG. 8 is an elevational view in section of the combined device of FIG. 6 showing a compressed soft bulb.
Figure 9:
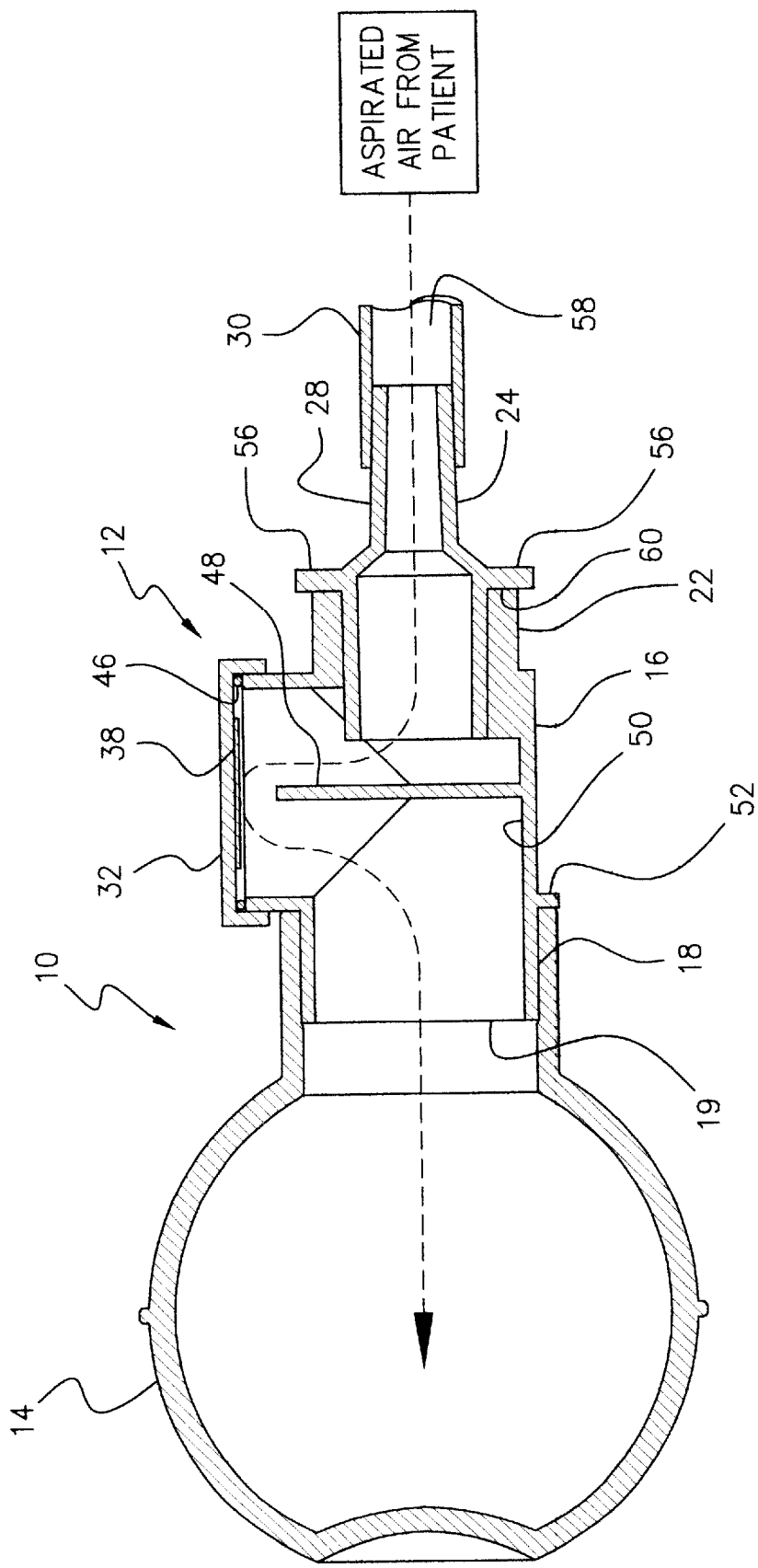
FIG. 9 is an elevational view in section of the combined device of FIG. 6 along line 7—7 showing the route of a patient's aspirated air past the $CO_2$ detector when the compressed bulb is released.

In operation shown in FIGS. 8 and 9, after the intubation tube is placed in the patient's trachea, bulb 14 is squeezed to force air out prior to attaching the housing 16 to the adapter 24. In the event that the intubation tube is properly placed into the trachea, as the trachea is substantially rigid, air is able to be aspirated from the trachea and the bulb 14 is able to freely re-expand. In addition, the air aspirated from the trachea, containing up to five percent $CO_2$, will pass over baffle 48 and change the color of the colorimetric indicator paper 38, which is fully exposed because backing paper 42 has been pulled out through second port 26 as shown in FIGS. 4 and 5.

In the event that the intubation tube is improperly placed into the esophagus, as the esophagus has no intrinsic structure to maintain rigidity, the esophagus will collapse due to the vacuum created by the compressed bulb 14, thus blocking and sealing the distal end of the intubation tube 30. The bulb 14 will remain in a compressed state due to the internal partial vacuum. In addition, no aspirated air containing $CO_2$ will pass over baffle 48 and the color of the colorimetric indicator paper will remain unchanged, therefore warning the caregiver that the intubation tube 30 is not in the trachea and should immediately be reinserted. Absent the use of the colorimetric indicator paper 38 it sometimes occurs that even though the intubation tube 30 is wrongly placed in the esophagus, the bulb 14 reinflates because of a leak, suggesting that the tube is properly placed. The use of the colorimetric indicator paper 38 is therefore a fail-safe method of confirming the proper placement of the intubation tube 30.

The components of the invention except for the bulb 14 and O-ring 46 are made of plastic with the disc made of clear plastic although it could be made of clear glass. The remaining components may or may not be made out of the clear plastic. The indicator paper backing 40 and 42 can be any acceptable commercial grade backing paper with a colorimetric indicator 38 such as described in U.S. Pat. Nos. 5,005,572 and 5,965,061, incorporated herein by reference.

The above description has described specific structural details of the combination $CO_2$ detector and esophageal detector of this invention. However, it will be within one having ordinary skill in the art to make modifications without departing from the spirit and scope of the underlying invention's inventive concept. The inventive concept is not limited to the structure described, but includes such modifications as would be considered equivalent.

Having thus described the invention, what is claimed and desired to be secured by Letters Patent is:

1. An esophageal detector device in combination with a carbon dioxide ($CO_2$) detector, the device and detector comprising:

an esophageal detector housing containing a first port connected to an elastomeric bulb, and a second port adapted for receipt of a first end of an intubation tube adapter and a third port between the first and second port; and a disc overlaying a chemically treated colorimetric indicator paper and a support for the disc affixed to the third port.

2. The esophageal detector device in combination with the $CO_2$ detector according to claim 1 wherein a baffle is integral with an interior surface of the esophageal detector housing below the third port.

3. The esophageal detector device in combination with the $CO_2$ detector according to claim 1 wherein the disc is a clear plastic affixed to a rim with the colorimetric indicator paper glued to a bottom surface of the disc.

4. The esophageal detector device in combination with the $CO_2$ detector according to claim 3 wherein an O-ring is positioned between the rim of the clear plastic disc and a rim of the third port.

5. The esophageal detector device in combination with the $CO_2$ detector according to claim 1 wherein the esophageal detector housing is cylindrical in shape and the first and second port are in axial alignment with each other.

6. The esophageal detector device in combination with the $CO_2$ detector according to claim 1 wherein the indicator paper is partially covered with a backing paper prior to use, the backing paper protruding through the second port in the esophageal detector device and being removed by pulling on the protruding backing paper to fully expose the indicator paper.

7. A carbon dioxide ($CO_2$) detector for use in combination with an esophageal detector, the $CO_2$ detector portion comprising:

a clear plastic disc seated on a rim affixed to the rim of a third port on a housing of the esophageal detector, the esophageal detector having a first and second port on each side distal from the third port, a top surface of a colorimetric indicator paper affixed to a bottom surface of the clear plastic disc and a backing paper remaining on a bottom surface of the indicator paper, the backing paper protruding out of the second port on the esophageal detector and an elastomeric bulb attached to the first port of the esophageal detector, the backing paper having been pulled out of the second port prior to attachment of an intubation tube adapter to the second port.

8. The $CO_2$ detector and esophageal detector according to claim 7 wherein the $CO_2$ detector rim is snap-fit to the third port.

9. The $CO_2$ detector and esophageal detector according to claim 7 wherein the $CO_2$ detector rim is heat welded to the third port.

10. The $CO_2$ detector and esophageal detector according to claim 7 wherein the $CO_2$ detector rim is glued to the third port.

11. The $CO_2$ detector and intubation device according to claim 7 wherein a baffle is mounted on an inner surface of the esophageal detector housing and positioned to rise vertically to slightly below the indicator paper at the third port.

12. The $CO_2$ detector and esophageal detector according to claim 7 wherein a flange on an outer surface of the adapter engages an outer edge of the esophageal detector housing and a flange on the esophageal detector housing engages an edge of an opening to the elastomeric bulb.

13. The $CO_2$ and esophageal detector device according to claim 7 wherein the esophageal detector housing is cylindrical in shape.

14. The $CO_2$ detector and esophageal detector according to claim 7 wherein the first and second port on the esophageal detector device are in axial alignment.

15. An esophageal detector device in combination with a carbon dioxide ($CO_2$) detector, the device and detector comprising:
   an esophageal detector housing containing a first port connected to an elastomeric bulb, and a second port adapted for receipt of a first end of an intubation tube adapter and a third port between the first and second port;
   a disc overlaying a chemically treated colorimetric indicator paper and a support for the disc affixed to the third port; and
   the intubation tube adapter affixed at a first end to the second port and affixed at a second end to an intubation tube.

* * * * *